United States Patent
Watanabe (10) Patent No.: US 9,347,830 B2
(45) Date of Patent: May 24, 2016

(54) APPARATUS AND METHOD FOR OBTAINING SPECTRAL IMAGE

(71) Applicant: OLYMPUS CORPORATION, Tokyo (JP)

(72) Inventor: Toshiaki Watanabe, Tokyo (JP)

(73) Assignee: OYMPUS CORPORATION, Tokyo (JP)

( * ) Notice: Subject to any disclaimer, the term of this patent is extended or adjusted under 35 U.S.C. 154(b) by 9 days.

(21) Appl. No.: 14/097,360

(22) Filed: Dec. 5, 2013

(65) Prior Publication Data

US 2014/0092390 A1    Apr. 3, 2014

Related U.S. Application Data

(63) Continuation of application No. PCT/JP2012/064460, filed on Jun. 5, 2012.

(30) Foreign Application Priority Data

Jun. 28, 2011  (JP) ................. 2011-142816

(51) Int. Cl.
  *G01J 3/45* (2006.01)
  *G01J 3/28* (2006.01)
  *G01J 3/26* (2006.01)
  *G01N 21/64* (2006.01)

(52) U.S. Cl.
  CPC ............ *G01J 3/2823* (2013.01); *G01J 3/26* (2013.01); *G01N 21/6456* (2013.01); *G01N 2021/6423* (2013.01)

(58) Field of Classification Search
  CPC ............. G01J 3/26; G01J 3/28; G01J 3/2823
  USPC ............................................. 356/454, 456
  See application file for complete search history.

(56) References Cited

U.S. PATENT DOCUMENTS

2008/0186508 A1*  8/2008  Kiesel et al. ................. 356/519

FOREIGN PATENT DOCUMENTS

| JP | 08-285688 A | 11/1996 |
| JP | 09-033345 A | 2/1997 |
| JP | 2006-084425 A | 3/2006 |
| JP | 2006-343686 A | 12/2006 |
| JP | 2010-249808 A | 11/2010 |

OTHER PUBLICATIONS

International Search Report dated Jul. 10, 2012 issued in PCT/JP2012/064460.

* cited by examiner

*Primary Examiner* — Jonathan Hansen
(74) *Attorney, Agent, or Firm* — Scully, Scott, Murphy & Presser, P.C.

(57) ABSTRACT

An apparatus for obtaining spectral image includes a variable spectral element capable of changing its spectral characteristics, a transmission wavelength setting unit for setting a wavelength of light to be transmitted by the variable spectral element, a variable spectral element control unit changing a first control of the variable spectral element and a second control of the variable spectral element for controlling spectral characteristics of the variable spectral element to each other, an image capturing unit capturing an image that is formed by light transmitted by the variable spectral element, and an image correction unit acquiring a difference image between a first image captured in the first control and a second image captured in the second control.

20 Claims, 6 Drawing Sheets

APPARATUS AND METHOD FOR OBTAINING SPECTRAL IMAGE

This application claims benefits of Japanese Patent Application No. 2011-142816 filed in Japan on Jun. 28, 2011, the contents of which are hereby incorporated reference.

BACKGROUND OF THE INVENTION

1. Field of the Invention

This invention relates to a spectral image-obtaining apparatus for obtaining object images with desired wavelengths in observation apparatuses, for example, such as endoscopes, microscopes, and surveillance cameras and relates to a method for obtaining spectral image.

2. Description of the Related Art

In recent years, a method in which spectral images are acquired with specific wavelengths in accordance with uses in observation and the acquired spectral images are displayed on a display device to be observed has been used for observations with observation apparatus such as endoscopes.

For example, so-called "special light observation" has been widely used for the sake of early detection of minute legion such as cancer or for the sake of detailed diagnosis of lesion area before surgery, and, in the special light observation, the particular structures of tissues are highlighted and are displayed by performing light wavelength control that is different from that for normal light observation.

Methods of special light observation includes: narrowband imaging (NBI) in which capillaries in the superficial layer of mucous membrane are highlighted and displayed by acquiring images formed by narrow band light of about 400 nm that is easily absorbed by hemoglobin in blood, or vessels in the middle layer of a tissue are highlighted and displayed by acquiring images formed by narrow band light of about 550 nm that is easily absorbed by hemoglobin; and near-infrared fluorescence observation in which deep vessels are observed by acquiring images formed by near-infrared fluorescence of about 850 nm that occurs in irradiation of near-infrared excitation light of about 800 nm to fluorescent substances such as indocyanine green (ICG) which are intravenously injected, for example.

For example, an etalon-type spectral element disclosed in Japanese Patent TOKUKAI No. 2002-148528 is publically known as a conventional optical element for obtaining spectral image. The etalon-type spectral element is a variable spectral transmittance element in which a reflexive film is provided on each of a pair of substrates made of light-transmitting material. And, the etalon-type spectral element can transmit light of a particular wavelength according to a distance between the substrates each having the reflexive film.

SUMMARY OF THE INVENTION

An apparatus for obtaining spectral image according to the present invention is characterized in that the apparatus includes: a variable spectral element having a pair of optical substrates that are placed opposite each other on an optical path of light from an object to be photographed, the variable spectral element being capable of changing its spectral characteristics by changing at least one of a distance between surfaces of the optical substrates and angles of inclinations of the optical substrates; a transmission wavelength setting unit for setting a wavelength of light to be transmitted by the variable spectral element in a range of wavelengths of light from the object; a variable spectral element control unit changing a first control of the variable spectral element and a second control of the variable spectral element to each other by changing a distance between the surfaces of the optical substrates or angles of inclinations of the optical substrates, the variable spectral element being controlled in the first control to have a transmission peak that exists near a wavelength set by the transmission wavelength setting unit, as its spectral characteristic, and the variable spectral element being controlled in the second control to have a transmission peak that does not exist in the range of the wavelengths of the light from the object, as its spectral characteristic; an image capturing unit capturing an image that is formed by light transmitted by the variable spectral element; and an image correction unit acquiring a difference image between a first image captured by the image capturing unit in the first control performed by the variable spectral element control unit and a second image captured by the image capturing unit in the second control performed by the variable spectral element control unit.

Also, in an apparatus for obtaining spectral image according to the present invention, it is preferred that the variable spectral element control unit controls the variable spectral element in the second control to incline the pair of the optical substrates at predetermined angles of the inclinations of the optical substrates at which the optical substrates are not parallel to each other so that the transmission peak of the variable spectral element disappears from a range of wavelengths of light from the object, respectively.

Also, in an apparatus for obtaining spectral image according to the present invention, it is preferred that the variable spectral element control unit controls the variable spectral element in the second control to widen a distance between the surfaces of the pair of the optical substrates to a predetermined distance so that the transmission peak of the variable spectral element disappears from a range of wavelengths of light from the object.

Also, in apparatus for obtaining spectral image according to the present invention, it is preferred that the variable spectral element control unit controls the variable spectral element in the second control to change a distance between the surfaces of the pair of the optical substrates and angles of inclinations of the optical substrates into a predetermined distance between the surfaces of and predetermined angles of inclinations of the optical substrates respectively so that the transmission peak of the variable spectral element shifts to a predetermined range of wavelengths out of a range of wavelengths of light from the object.

Also, in an apparatus for obtaining spectral image according to the present invention, it is preferred that: the apparatus includes an image shift detecting unit detecting an amount of a difference between a position of the object in a standard image and a position of the object in a first image captured by the image capturing unit after capturing the standard image, the standard image being a first image that is captured by the image capturing unit for the first time after capturing a second image; and the variable spectral element control unit changes the first control of the variable spectral element to the second control of the variable spectral element when the amount of the difference between the positions of the object in those images detected by the image shift detecting unit is beyond a predetermined threshold, and the variable spectral element control unit changes the second control to the first control after the image capturing unit captures a second image.

Also, in an apparatus for obtaining spectral image according to the present invention, it is preferred that the variable spectral element control unit changes the first control of the variable spectral element and the second control of the variable spectral element to each other with timing at which the image capturing unit can capture first images and second images alternately the first images with the second images.

Also, in an apparatus for obtaining spectral image according to the present invention, it is preferred that: the apparatus includes a unit for setting timing for obtaining second image by which timing for capturing first images and second images respectively by the image capturing unit is set; and the variable spectral element control unit synchronizes with timing which is set by the unit for setting timing for obtaining second image, to change the first control of the variable spectral element and the second control of the variable spectral element to each other.

Also, a method for obtaining spectral image according to the present invention, in which an image is obtained by changing control of a variable spectral element having a pair of optical substrates that are placed opposite each other on an optical path of light from an object to be photographed, the variable spectral element being capable of changing its spectral characteristics by changing at least one of a distance between surfaces of the optical substrates and angles of inclinations of the optical substrates, is characterized in that: a wavelength of light to be transmitted by the variable spectral element in a range of wavelengths of light from the object is set; a first control of the variable spectral element and a second control of the variable spectral element are changed to each other by changing the distance between the surfaces of the optical substrates or the angles of inclinations of the optical substrates, the variable spectral element being controlled in the first control to have a transmission peak that exists near the set wavelength, as its spectral characteristic, and the variable spectral element being controlled in the second control to have a transmission peak that does not exist in the range of the wavelengths of the light from the object, as its spectral characteristic; an image formed by light that is transmitted by the variable spectral element in each of the first control and the second control is captured; and a difference image between a first image captured in the first control of the variable spectral element and a second image captured in the second control of the variable spectral element is captured.

Also, in a method for obtaining spectral image according to the present invention, it is preferred that, in the second control of the variable spectral element, the pair of the optical substrates are inclined at predetermined angles of the inclinations of the optical substrates at which the pair of the optical substrates are not parallel to each other so that transmission peak of the variable spectral element disappears from a range of wavelengths of light from the object, respectively.

Also, in a method for obtaining spectral image according to the present invention, it is preferred that, in the second control of the variable spectral element, a distance between the surfaces of the pair of the optical substrates is widened to a predetermined distance so that transmission peak of the variable spectral element disappears from a range of wavelengths of light from the object.

Also, in a method for obtaining spectral image according to the present invention, it is preferred that, in the second control of the variable spectral element, a distance between the surfaces of the optical substrates and angles of inclinations of the optical substrates are controlled to change into a predetermined distance and predetermined angles respectively so that a transmission peak of the variable spectral element shifts to a predetermined range of wavelengths out of a range of wavelengths of light from the object.

Also, in a method for obtaining spectral image according to the present invention, it is preferred that: an amount of a difference between a position of the object in a standard image and a position of the object in a first image captured after capturing the standard image is detected, the standard image being a first image that is captured for the first time after capturing a second image; and the first control of the variable spectral element is changed to the second control of the variable spectral element so that a second image is captured when the detected amount of the difference between the positions of the object in those images is beyond a predetermined threshold, and the second control is changed into the first control after capturing the second image.

Also, in a method for obtaining spectral image according to the present invention, it is preferred that the first control of the variable spectral element and the second control of the variable spectral element are changed to each other with timing at which first images and second images can be captured alternately the first images with the second images.

Also, in a method for obtaining spectral image according to the present invention, it is preferred that: timing with which first images and second images are captured respectively is set; and the first control of the variable spectral element and the second control of the variable spectral element are changed to each other while the change of the first control and second control to each other is being synchronizing with the set timing.

These and other features and advantages of the present invention will become apparent from the detailed description of the preferred embodiments when taken in conjunction with the accompanying drawings.

BRIEF DESCRIPTION OF THE DRAWINGS

FIGS. 3A to 3F are explanatory views showing one example of optical characteristics in a special light observation using an endoscope provided with an apparatus for obtaining spectral image with which a method for obtaining spectral image according to the embodiment 1 of the present invention is performed.

FIGS. 4A to 4E are explanatory views showing one example of optical characteristics in a special light observation using an endoscope provided with an apparatus for obtaining spectral image with which a method for obtaining spectral image according to a variation example 1 of the embodiment 1 of the present invention is performed.

FIGS. 5A to 5C are explanatory views showing one example of optical characteristics in a special light observation using an endoscope provided with an apparatus for obtaining spectral image with which a method for obtaining spectral image according to a variation example 2 of the embodiment 1 of the present invention is performed.

FIGS. 6A and 6C are explanatory views showing one example of optical characteristics in a special light observation using an endoscope provided with an apparatus for obtaining spectral image with which a method for obtaining spectral image according to a variation example 3 of the embodiment 1 of the present invention is performed.

FIGS. 7A to 7C are explanatory views showing one example of optical characteristics in a special light observation using an endoscope provided with an apparatus for obtaining spectral image with which a method for obtaining spectral image according to a variation example 4 of the embodiment 1 of the present invention is performed.

DETAILED DESCRIPTION OF THE PREFERRED EMBODIMENTS

Prior to the explanation about the embodiments, operation effects of the present invention are explained.

An apparatus for obtaining spectral image according to the present invention includes: a variable spectral element having a pair of optical substrates that is placed opposite each other on an optical path of light from an object to be photographed, the variable spectral element being capable of changing its spectral characteristics by changing at least one of a distance between the surfaces of the optical substrates and angles of inclinations of the optical substrates; a transmission wavelength setting unit for setting a wavelength of light to be transmitted by the variable spectral element in a range of wavelengths of the light from the object; a variable spectral element control unit changing a first control of the variable spectral element and a second control of the variable spectral element to each other by changing the distance between the surfaces of the optical substrates or the angles of the inclinations of the optical substrates, the variable spectral element being controlled in the first control to have a transmission peak that exists near a wavelength set by the transmission wavelength setting unit, as its spectral characteristic, and the variable spectral element being controlled in the second control to have a transmission peak that does not exist in the range of the wavelengths of the light from the object, as its spectral characteristic; an image capturing unit capturing an image that is formed by light that is transmitted by the variable spectral element; and an image correction unit acquiring a difference image between a first image captured by the image capturing unit in the first control performed by the variable spectral element control unit and a second image captured by the image capturing unit in the second control performed by the variable spectral element control unit.

As described above, etalon-type spectral elements inevitably transmit not only light of a desired wavelength but also a predetermined slight amount of light except the light of the desired wavelength (for example, about 1%) when the etalon-type spectral elements transmits the light of the desired wavelength.

However, the present inventor examined and analyzed the relation between: a distance between of the surfaces of and angles of inclinations of a pair of optical substrates constituting an etalon-type spectral element; and leak light. As a result, the present inventor found that the approximately same amount of leak light occurs throughout the approximately same wavelength range both: in the cases of a distance between the surfaces of and angles of inclinations of the optical substrates with which its transmission peak does not exist; and in the cases of a predetermined distance between the surfaces of and predetermined angles of inclinations of the optical substrates with which its transmission peak exists.

Accordingly, the present inventor came up with the present invention in which spectral images are corrected in such a way that: a variable spectral element control unit changes a first control of the variable spectral element and a second control of the variable spectral element to each other, a variable spectral element being controlled in the first control to have a transmission peak that exists near a wavelength set by a transmission wavelength setting unit, as its spectral characteristic, and the variable spectral element being controlled in the second control to have no transmission peak that exists in a range of wavelengths of light from the object, as its spectral characteristic; and an image correction unit acquires a difference image between a first image captured by the image capturing unit in the first control performed by the variable spectral element control unit and a second image captured by the image capturing unit in the second control performed by the variable spectral element control unit.

An apparatus and a method for obtaining spectral image according to the present invention make it possible to obtain spectral images with desired wavelengths and with a high S/N ratio while influences of leak light are being reduced to the utmost.

Figure 1:
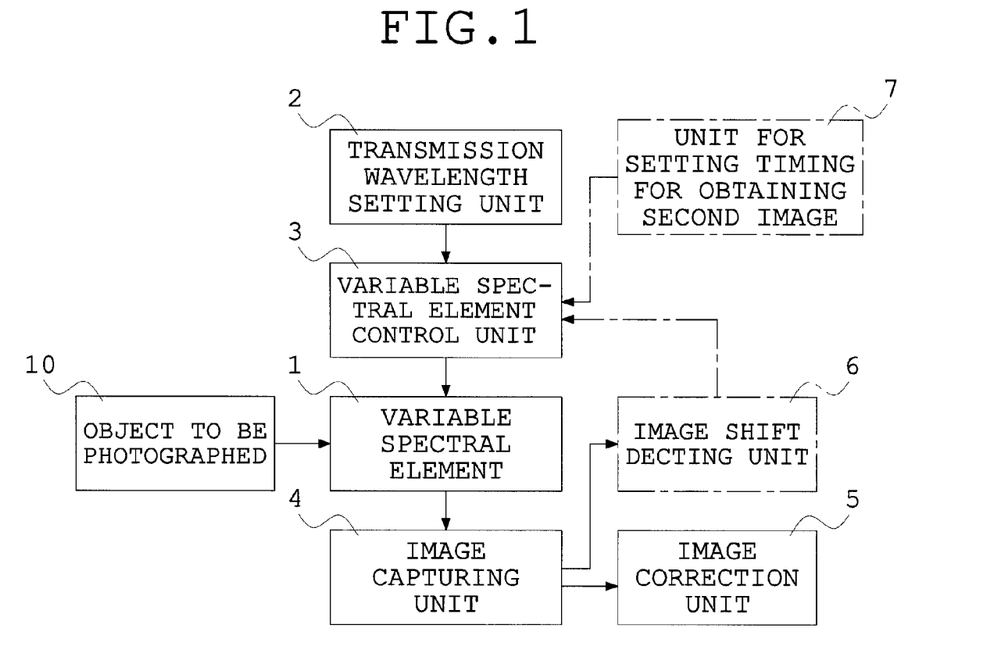
FIG. 1 is a block diagram schematically showing the whole structure of an apparatus for obtaining spectral image with which a method for obtaining spectral image according to one embodiment of the present invention is performed.

FIG. 1 is a block diagram schematically showing the whole structure of an apparatus for obtaining spectral image with which a method for obtaining spectral image according to one embodiment of the present invention is performed.

An apparatus for obtaining spectral image shown in FIG. 1 includes a variable spectral element 1, a transmission wavelength setting unit 2, a variable spectral element control unit 3, an image capturing unit 4, and an image correction unit 5. Besides, a reference numeral 10 shown in FIG. 1 denotes an object to be photographed, such as living tissues.

The variable spectral element 1 is configured as an etalon-type variable spectral element which includes a pair of optical substrates placed opposite each other on an optical path of light from an object 10 to be photographed and the spectral characteristics of which can be changed by changing at least one of a distance between the surfaces of the optical substrates and angles of inclinations of the optical substrates.

The transmission wavelength setting unit 2 is configured so that a user can make an on-screen input to set a wavelength of light transmitted by the variable spectral element 1 in a range of wavelengths of the light from the object 10, for example.

The variable spectral element control unit 3 is configured to be capable of changing the first control of the variable spectral element and the second control of the variable spectral element to each other by changing a distance between the surfaces of the pair of the optical substrates or angles of inclinations of the optical substrates, the variable spectral element 1 being controlled in the first control to have a transmission peak that exists near a wavelength set by the transmission wavelength setting unit 2, as its spectral characteristic, and the variable spectral element 1 being controlled in the second control to have a transmission peak that does not exist in the range of the wavelengths of the light from the object 10, as its spectral characteristic.

More minutely, the variable spectral element control unit 3 controls a distance between the surfaces of the pair of the optical substrates with the surfaces of the optical substrates kept parallel to each other, in the first control of the variable spectral element, so that the variable spectral element 1 has a transmission peak that exists near a wavelength set by the transmission wavelength setting unit 2, as its spectral characteristic.

Also, the variable spectral element control unit 3 controls at least one of a distance between the surfaces of the optical substrates and angles of inclinations of the optical substrates, in the second control of the variable spectral element, so that the variable spectral element 1 has a transmission peak that does not exist in the range of the wavelengths of the light from the object 10, as its spectral characteristic.

The image capturing unit 4 includes a solid-state image sensing device such as CCD and CMOS for example and is configured to capture an image that is formed by light transmitted by the variable spectral element 1.

The image correction unit 5 acquires a difference between: a first image captured by the image capturing unit 4 in the first control performed by the variable spectral element control unit 3; and a second image captured by the image capturing unit 4 in the second control performed by the variable spectral element control unit 3.

A method of obtaining spectral image using the apparatus for obtaining spectral image having such a structure and shown in FIG. 1 in the case where images of an object to be photographed are captured with light of desired wavelengths is explained. A user first sets the apparatus to a desired wavelength of light transmitted by the variable spectral element 1, through the transmission wavelength setting unit 2. Information on the wavelength set through the transmission wavelength setting unit 2 is sent to the variable spectral element control unit 3.

The variable spectral element control unit 3 changes the first control of the variable spectral element and the second control of the variable spectral element to each other with predetermined timing, to perform the first control or the second control, where a distance between the surfaces of the pair of the optical substrates is controlled with the optical substrates kept parallel to the each other in the first control so that the variable spectral element 1 has a transmission peak that exists near a wavelength set through the transmission wavelength setting unit 2, as its spectral characteristic, and at least one of a distance between the surfaces of the pair of the optical substrates and angles of inclinations of the optical substrates is controlled in the second control so that the variable spectral element 1 has a transmission peak that does not exist in the range of the wavelengths of the light from the object 10, as its spectral characteristic.

Light traveling from the object 10 enters the variable spectral element 1.

In this case, when the variable spectral element control unit 3 performs the first control of the variable spectral element, the surfaces of the pair of the optical substrates of the variable spectral element 1 is kept at a predetermined distance while the optical substrates are being kept parallel to each other so that the variable spectral element 1 has a transmission peak that exists near a wavelength set through the transmission wavelength setting unit 2, as its spectral characteristic. The variable spectral element 1 which is in such a state transmits not only light the wavelength of which is set by the transmission wavelength setting unit 2 but also leak light the wavelengths of which differ from the wavelength set by the transmission wavelength setting unit 2.

Also, when the variable spectral element control unit 3 performs the second control of the variable spectral element, a predetermined distance between the surfaces of and predetermined angles of inclinations of the pair of the optical substrates of the variable spectral element 1 are kept so that the variable spectral element 1 has a transmission peak that does not exist in the range of the wavelengths of the light from the object 10, as its spectral characteristic. The variable spectral element 1 which is in such a state transmits the approximately same leak light as variable spectral element 1 does in the first control performed by the variable spectral element control unit 3, and the amount of the leak light transmitted by the variable spectral element 1 in the second control is approximately equal to that of the leak light transmitted by the spectral element 1 in the first control.

Light transmitted by the variable spectral element 1 enters the image capturing unit 4. And then, the image capturing unit 4 acquires an image of the object to be photographed.

Besides, images which are captured by the image capturing unit 4 in the first control performed by the variable spectral element control unit 3 are called first image (spectral image), and images which are captured by the image capturing unit 4 in the second control performed by the variable spectral element control unit 3 are called second image (reference image).

A first image contains components of light of a desired wavelength set by the transmission wavelength setting unit 2 and components of leak light having wavelengths different from that of the light transmitted by the transmission wavelength setting unit 2. Also, a second image contains the approximately same components as those of the leak light which are contained in the first image, and the amounts of the components of the leak light contained in the second image are approximately equal to those of the components of the leak light contained in the first image respectively.

The image correction unit 5 acquires a difference between the first and second images. The components of the leak light are almost removed from the acquired difference image.

As a result, the apparatus for obtaining spectral image shown in FIG. 1 and the above-described method for obtaining spectral image reduce the influence of leak light to the utmost and are make it possible to obtain spectral images formed by light of desired wavelengths at a high S/N ratio.

Besides, in the apparatus for obtaining spectral image shown in FIG. 1 and the above-described method for obtaining spectral image, it is preferred that the variable spectral element control unit 3 controls the variable spectral element 1 in the second control in such a way that the pair of the optical substrates are inclined at predetermined angles of inclinations of the optical substrates at which the optical substrates are not parallel to each other so that the transmission peak of the variable spectral element 1 disappears from the range of the wavelengths of the light from the object 10, respectively.

Alternatively, in the apparatus for obtaining spectral image shown in FIG. 1 and the above-described method for obtaining spectral image, the variable spectral element control unit 3 may control the variable spectral element 1 in the second control in such a way that a distance between the surfaces of the pair of the optical substrates is widened to a predetermined distance so that the transmission peak of the variable spectral element 1 disappears from the range of the wavelengths of the light from the object 10.

Alternatively, in the apparatus for obtaining spectral image shown in FIG. 1 and the above-described method for obtaining spectral image, the variable spectral element control unit 3 may control the variable spectral element 1 in the second control in such a way that a distance between the surfaces of the pair of the optical substrates and angles of inclinations of the optical substrates are changed to a predetermined distance between the surfaces of and predetermined angles of the inclinations of the optical substrates respectively so that the transmission peak of the variable spectral element 1 shifts to a predetermined range of wavelengths out of the range of the wavelengths of the light from the object 10.

Also, in the apparatus for obtaining spectral image shown in FIG. 1 and the above-described method for obtaining spectral image, it is preferred that: the apparatus further includes an image shift detecting unit 6 detecting an amount of a difference between a position of the object 10 in a standard image and a position of the object 10 in a first image captured by the image capturing unit 4 after capturing the standard image, the standard image being a first image that is captured by the image capturing unit 4 for the first time after capturing a second image; and the variable spectral element control unit 3 changes the first control of the variable spectral element to the second control of the variable spectral element when the amount of the difference between the positions of the object 10 which is detected by the image shift detecting unit 6 is beyond a predetermined threshold, and the variable spectral element control unit 3 changes the second control to the first control after the image capturing unit 4 captures a second image.

For example, in special light observation using an endoscope, a couple of dozen images are usually captured in one second. In the case where the object 10 moves slowly, the position of the object 10 does not vary in a plurality of images. In order to increase a frame rate at which the object 10 is observed, it is desirable to increase the number of first images (spectral image) to the utmost among the plurality of the images in which the position of the object 10 does not vary. On the other hand, a single second image (reference image) is sufficient for this observation.

Accordingly, as described above, the apparatus for obtaining spectral image is provided with the image shift detecting unit 6, and the apparatus is operated in such a way that: the variable spectral element control unit 3 changes the first control of the variable spectral element to the second control of the variable spectral element when an amount of a difference between the positions of the object 10 detected by the image shift detecting unit 6 is beyond a predetermined threshold; and the variable spectral element control unit 3 changes the second control to the first control after the image capturing unit 4 captures a second image.

Such a manner makes it possible to obtain spectral images with desired wavelengths at a high frame rate, with high efficiency, and at a high S/N ratio.

Besides, in the apparatus for obtaining spectral image shown in FIG. 1 and the above-described method for obtaining spectral image, the variable spectral element control unit 3 may change the first control of the variable spectral element and the second control of the variable spectral element to each other with timing at which the image capturing unit 4 can capture first images and second images alternately the first images with the second images.

Such a manner makes it possible to absolutely obtain spectral images with desired wavelengths at a high S/N ratio also in the case where the object 10 moves fast.

Also, in the apparatus for obtaining spectral image shown in FIG. 1 and the above-described method for obtaining spectral image, the apparatus includes a unit 7 for setting timing for obtaining second image by which a user sets timing with which the image capturing unit 4 captures first images and second images respectively, and the variable spectral element control unit 3 may synchronize with timing which is set by the unit 7 for setting timing for obtaining second image, to change the first control of the variable spectral element and the second control of the variable spectral element to each other.

Such a manner makes it possible to obtain spectral images with desired wavelengths efficiently and at a high S/N ratio in accordance with various observation uses.

Next, embodiments of an apparatus for obtaining spectral image and a method for obtaining spectral image according to the present invention are explained. Besides, a structure of an apparatus for obtaining spectral image which is used for endoscopes is explained in the below embodiments, for the sake of convenience.

Figure 2:
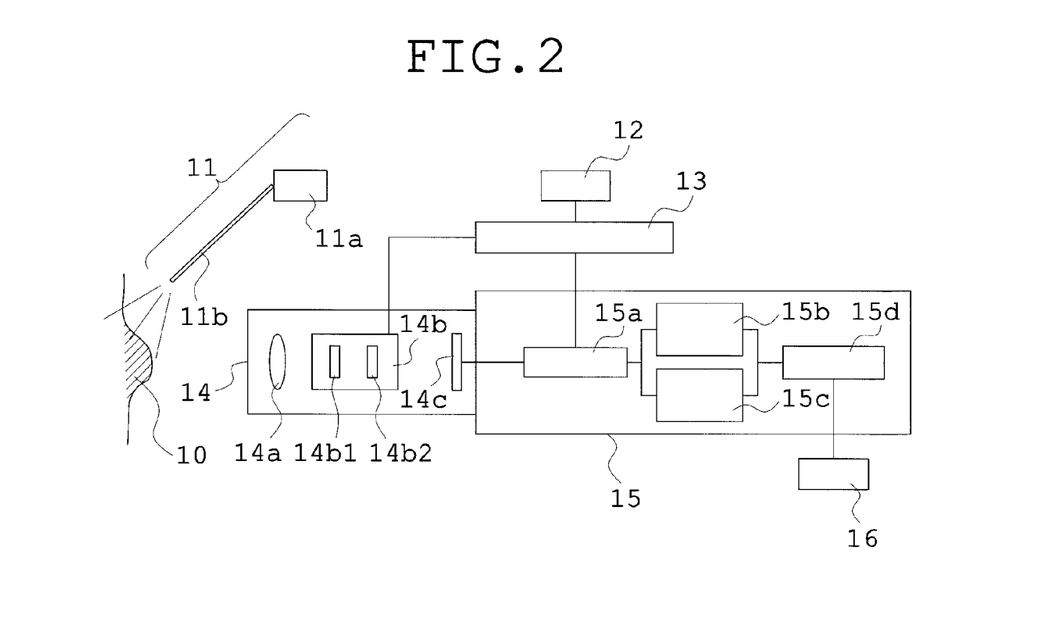
FIG. 2 is a block diagram showing a structure common to endoscopes provided with spectral image obtaining apparatuses with which methods for obtaining spectral image according to embodiments of the present invention are performed respectively.

FIG. 2 is a block diagram showing a structure common to endoscopes provided with apparatuses for obtaining spectral image with which methods for obtaining spectral image according to the embodiments of the present invention are performed respectively, respectively.

An endoscope shown in FIG. 2 includes a light source unit 11, an input unit 12, a variable spectral element control unit 13, an imaging unit 14, an image-processing unit 15, and a display unit 16. Besides, a reference numeral 10 shown in FIG. 2 denotes a living tissue that is an object to be photographed.

The light source unit 11 is provided with a light source 11a, a light guide 11b, and so on, for example. The light source unit 11 is configured to irradiate light in a predetermined wavelength band range in accordance with uses in observation, such as a visible light wavelength band range and a near infrared excitation wavelength band range, to the object 10. Besides, it is presumed in the below embodiments that the light source unit 11 irradiates light in a predetermined visible light wavelength band range for the sake of convenience.

The input unit 12 includes an input screen which can be displayed on a display apparatus of a personal computer connected with the endoscope and through which an input can be made, for example. The input unit 12 has a function corresponding to that of the transmission wavelength setting unit 2 in the apparatus for obtaining spectral image which is shown in FIG. 1.

The variable spectral element control unit 13 is configured in the same manner as the variable spectral element control unit 3 for the apparatus for obtaining spectral image which is shown in FIG. 1.

The imaging unit 14 is provided with a lens 14a, a variable spectral element 14b, and an imaging sensor 14c.

The lens 14a forms an image of light from the object 10 on the imaging plane of the imaging sensor 14c.

The imaging sensor 14c is composed of CCD or CMOS for example, and the imaging sensor 14c captures an image formed by light that is transmitted by the variable spectral element 14b.

The variable spectral element 14b is placed on an optical path of light from the object 10. And, the variable spectral element 14b corresponds to the variable spectral element 1 for the apparatus for obtaining spectral image shown in FIG. 1, and the variable spectral element 14b is configured as an etalon-type variable spectral element having a structure in which: the variable spectral element 14b includes a pair of optical substrates 14b1 and 14b2 the surfaces of which are provided with dielectric multilayer films as a reflexive film respectively; and its spectral characteristics can be changed by changing a distance between the surfaces of or angles of inclinations of the optical substrates 14b1 and 14b2 through the variable spectral element control unit 13.

Besides, the etalon-type variable spectral element is a spectral device for which interference of light is used and by which a wavelength of light transmitted or reflected by the spectral device can be changed by changing a distance between a pair of mirror surfaces that are placed opposite each other.

The image-processing unit 15 is composed of: a central operation processing unit and a memory of the personal computer connected with the endoscope; and software. The image-processing unit 15 is provided with an image-forming unit 15a, a spectral image memory 15b, a reference image memory 15c, and an image operation unit 15d.

The image-forming unit 15a gives image signals captured by the imaging sensor 14c a predetermined image conversion process, to form an image.

And, in the apparatus for obtaining spectral image which is shown in FIG. 2, the imaging sensor 14c and the image-forming unit 15a correspond to the image capturing unit 4 for the apparatus for obtaining spectral image which is shown in FIG. 1.

The spectral image memory 15b is a memory region into which a first image (spectral image) captured by the imaging sensor 14c and the image-forming unit 15a in the first control performed by the variable spectral element control unit 13 is stored. The reference image memory 15c is a memory region into which a second image (reference image) captured by the imaging sensor 14c and the image-forming unit 15a in the second control performed by the variable spectral element control unit 13 is stored.

The image operation unit 15d corresponds to the image correction unit 5 for the apparatus for obtaining spectral image which is shown in FIG. 1. And, the image operation unit 15d calculates a difference between a predetermined first image stored in the spectral image memory 15b and a predetermined second image stored in the reference image memory 15c.

The display unit 16 is composed of a display device connected with the personal computer for example. And, an image obtained by an operation process performed by the image operation unit 15d is displayed on the display unit 16.

Embodiment 1

Figure 3A:
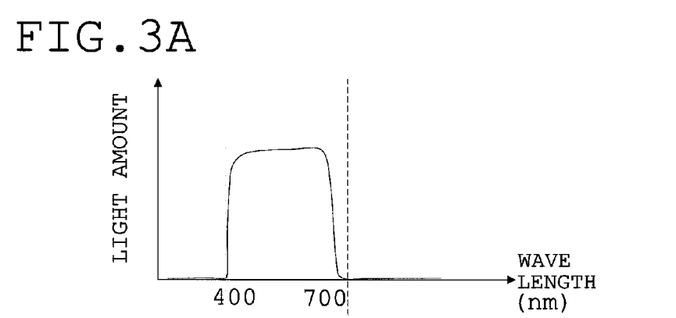
FIG. 3A is a graph showing spectra of illumination light.
Figure 3B:
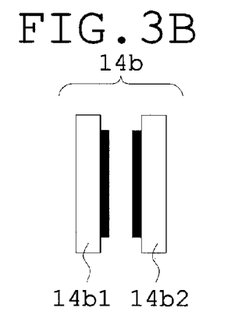
FIG. 3B is a view showing a distance between the surfaces of a pair of optical substrates and the angles of inclinations of the optical substrates in the first control of the variable spectral element, the optical substrates constituting a variable spectral element.
Figure 3C:
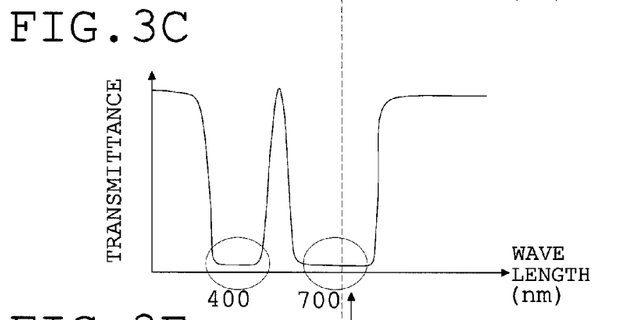
FIG. 3C is a graph showing a spectral transmittance of the variable spectral element in the first control.
Figure 3D:
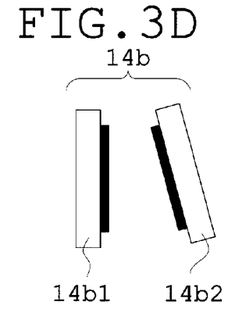
FIG. 3D is a view showing a distance between the surfaces of the pair of the optical substrates and the angles of inclinations of the optical substrates in the second control of the variable spectral element, the optical substrates constituting the variable spectral element.
Figure 3E:
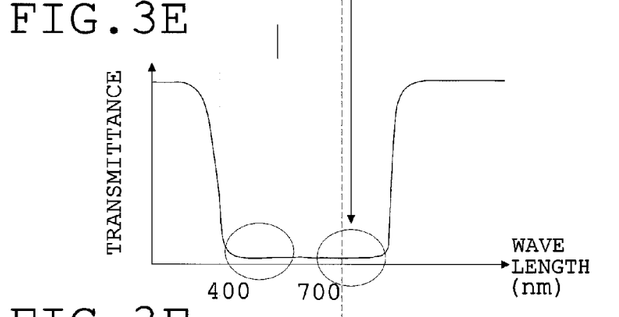
FIG. 3E is a graph showing a spectral transmittance of the variable spectral element in the second control.
Figure 3F:
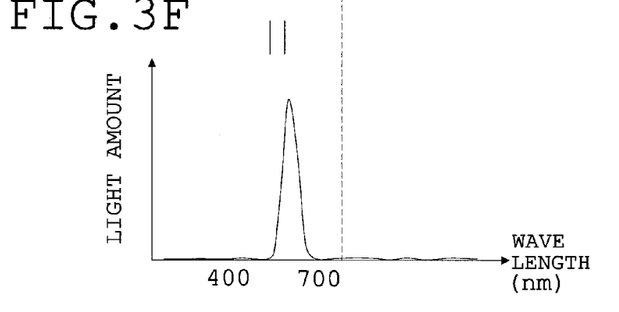
FIG. 3F is a graph showing spectra of a spectral image which is corrected by an image correction unit.

FIGS. 3A to 3F are explanatory views showing one example of optical characteristics in a special light observation using an endoscope provided with an apparatus for obtaining spectral image with which a method for obtaining spectral image according to the embodiment 1 of the present invention is performed, FIG. 3A is a graph showing spectra of illumination light, FIG. 3B is a view showing a distance between the surfaces of a pair of optical substrates and angles of inclinations of the optical substrates in the first control of the variable spectral element, the optical substrates constituting a variable spectral element, FIG. 3C is a graph showing a spectral transmittance of the variable spectral element in the first control, FIG. 3D is a view showing a distance between the surfaces of the pair of the optical substrates and angles of inclinations of the optical substrates in the second control of the variable spectral element, the optical substrates constituting the variable spectral element, FIG. 3E is a graph showing a spectral transmittance of the variable spectral element in the second control, and FIG. 3F is a graph showing spectra of a spectral image which is corrected by an image correction unit.

Besides, as described above, the fundamental structure shown in FIG. 2 is common to the below respective embodiments.

In an endoscope provided with the apparatus for obtaining spectral image according to the embodiment 1 of the present invention, the light source unit 11 includes a xenon light source and emits light in a visible wavelength band ranging from 400 nm to 700 nm, as shown in FIG. 3A.

The variable spectral element control unit 13 controls the variable spectral element 14b to separate the pair of the optical substrates 14b1 and 14b2 from each other at a predetermined distance while the optical substrates 14b1 and 14b2 of the variable spectral element 14b are being kept parallel to each other in the first control of the variable spectral element so that the variable spectral element 14b has a transmission peak with a predetermined half band width of 20 nm for example in a predetermined narrow band in a range of wavelengths of visible light reflected by the living tissue 10, as its spectral characteristic, as shown in FIGS. 3B and 3C, the range of the wavelengths of the visible light reflected by the living tissue 10 ranging from 400 nm to 700 nm. The imaging sensor 14c captures an image formed by light that is transmitted by the variable spectral element 14b in the first control performed by the variable spectral element control unit 13. The image-forming unit 15a gives signals captured by the imaging sensor 14c a predetermined image conversion process, to form a first image.

Also, the variable spectral element control unit 13 controls the variable spectral element 14b to incline the pair of the optical substrates 14b1 and 14b2 at predetermined angles respectively to make the optical substrates 14b1 and 14b2 of the variable spectral element 14b nonparallel to each other in the second control of the variable spectral element so that the variable spectral element 14b has a spectral characteristic in which its transmission peak disappears from the range of the wavelengths of visible light reflected by the object 10, as shown in FIGS. 3D and 3E, the range of the wavelengths of the visible light reflected by the object 10 ranging from 400 nm to 700 nm. The imaging sensor 14c captures an image formed by light that is transmitted by the variable spectral element 14b in the second control performed by the variable spectral element control unit 13. The image-forming unit 15a gives signals captured by the imaging sensor 14c a predetermined image conversion process, to form a second image. In the second control of the variable spectral element, images of only components of leak light are captured. Besides, in this case, the first control and second control performed by the variable spectral element control unit 13 are changed to each other as often as the imaging sensor 14c captures an image of one frame.

The image operation unit 15d calculates a difference between a gray level in each pixel of a first image captured by the imaging sensor 14c and the image-forming unit 15a in the first control performed by the variable spectral element control unit 13 and a gray level in each pixel of a second image captured by the imaging sensor 14c and the image-forming unit 15a in the second control performed by the variable spectral element control unit 13.

Gray levels caused by leak light in the second image captured in the second control of the variable spectral element are approximately equal to those caused by leak light in the first image captured in the first control of the variable spectral element. As a result, the gray levels caused by leak light are removed from the first image by taking a difference between the gray levels in the two images.

As a result, the apparatus for obtaining spectral image and the method for obtaining spectral image according to the embodiment 1 makes it possible to obtain spectral images with light in a narrow band range at a high S/N ratio, with components caused by leak light removed from these spectral images.

Besides, in the apparatus for obtaining spectral image and the method for obtaining spectral image according to the embodiment 1, the control of the variable spectral element 14b in the second control performed by the variable spectral element control unit 13 so as to make the variable spectral element 14b have optical characteristics in which its transmission peak does not exist in the range of the wavelengths of visible light reflected by the living tissue 10, the range of the wavelengths of the visible light reflected by the living tissue 10 ranging from 400 nm to 700 nm, is not limited to the example shown in FIG. 3. For example, the variable spectral element 14b may be controlled in the second control of the variable spectral element in a manner such as is next explained in a variation example 1, 2, or 3 of the embodiment 1 using FIGS. 4A to 4E, 5A to 5C, or 6A to 6C.

Variation Example 1

Figure 4A:
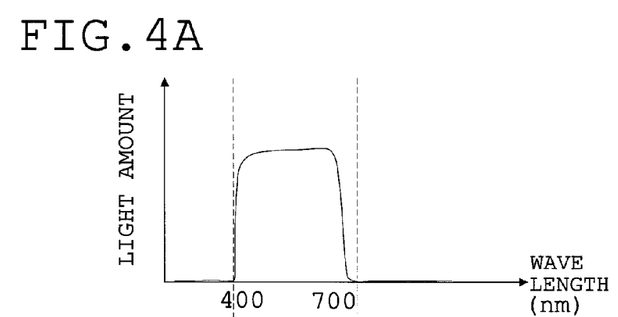
FIG. 4A is a graph showing spectra of illumination light.
Figure 4B:
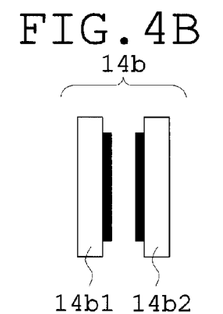
FIG. 4B is a view showing a distance between the surfaces of a pair of optical substrates and the angles of inclinations of the optical substrates in the first control of the variable spectral element, the optical substrates constituting a variable spectral element.
Figure 4C:
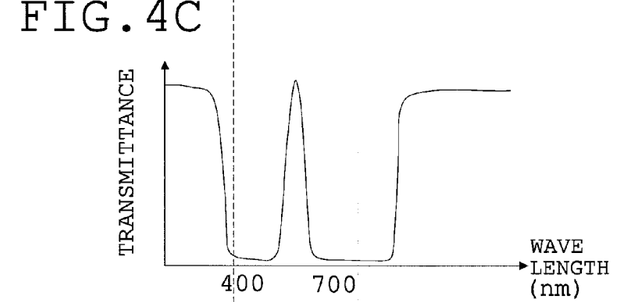
FIG. 4C is a graph showing a spectral transmittance of the variable spectral element in the first control.
Figures 4D, 4E:
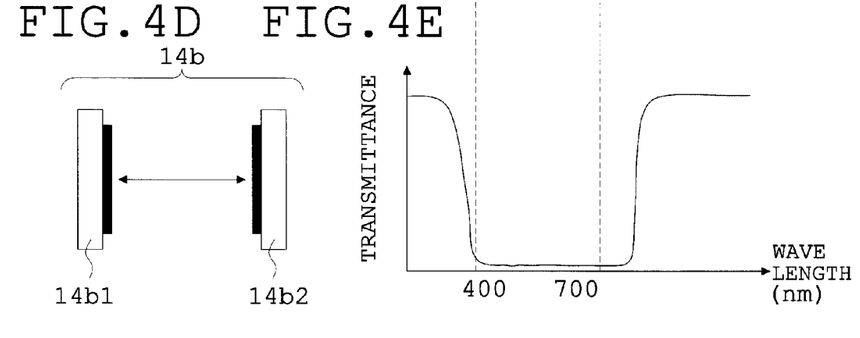
FIG. 4D is a view showing a distance between the surfaces of the pair of the optical substrates and the angles of inclinations of the optical substrates in the second control the variable spectral element, the optical substrates constituting the variable spectral element.
FIG. 4E is a graph showing a spectral transmittance of the variable spectral element in the second control.

FIGS. 4A to 4E are explanatory views showing one example of optical characteristics in a special light observation using an endoscope provided with an apparatus for obtaining spectral image with which a method for obtaining spectral image according to a variation example 1 of the embodiment 1 of the present invention is performed, FIG. 4A is a graph showing spectra of illumination light, FIG. 4B is a view showing a distance between the surfaces of a pair of optical substrates and angles of inclinations of the optical substrates in the first control of the variable spectral element, the optical substrates constituting a variable spectral element, FIG. 4C is a graph showing a spectral transmittance of the variable spectral element in the first control, FIG. 4D is a view showing a distance between the surfaces of the pair of the optical substrates and angles of inclinations of the optical substrates in the second control of the variable spectral element, the optical substrates constituting the variable spectral element, and FIG. 4E is a graph showing a spectral transmittance of the variable spectral element in the second control.

In the apparatus for obtaining spectral image and the method for obtaining spectral image according to the variation example 1, the variable spectral element control unit 13 is configured to control the variable spectral element 14b to separate the surfaces of the pair of the optical substrates 14b1 and 14b2 from each other at a predetermined distance (for example, at a distance of 10 μm) in the second control of the variable spectral element so that the transmission peak of the variable spectral element 14b disappears from a range of the wavelengths of visible light reflected by the object 10, the range of the wavelengths of the visible light reflected by the object 10 ranging from 400 nm to 700 nm.

In order to make the transmission peak of the variable spectral element 14b disappear from the range of the wavelengths of light from the object 10, the surfaces of the pair of the optical substrates 14b1 and 14b2 should be separated from each other at a distance larger than the coherence length in the range of the wavelengths of the light from the object 10 (in the range of the wavelengths of visible light ranging from 400 nm to 700 nm, in this case) while the optical substrates 14b1 and 14b2 are being kept parallel to each other. Light traveling from the object 10 is composed of plural types of light having various phases, these types of light are not in phase, and the coherence length is short. And, when the surfaces of the pair of the optical substrates 14b1 and 14b2 are separated from each other at a distance of a couple to tens of micrometers, the light components in the range of wavelengths of visible light ranging from 400 nm to 700 nm cannot resonate with one another, so that its transmission peak does not exists in the range of wavelengths from 400 nm to 700 nm.

Accordingly, light incident on the variable spectral element 14b can be intercepted except leak light even though the second control of the variable spectral element is performed by the variable spectral element control unit 13 as in the variation example 1. As a result, second images captured by the imaging sensor 14c and the image-forming unit 15a are formed only by the leak light, and gray levels caused by the leak light are removed from first images when the image operation unit 15d calculates a difference between gray levels in first and second images in each pixel.

The other constitution and operation effects in the present variation example are the approximately same as those of the apparatus and the method for obtaining spectral image of the embodiment 1.

Variation Example 2

Figure 5A:
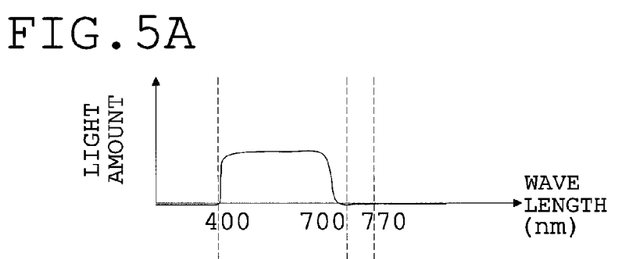
FIG. 5A is a graph showing spectra of illumination light.
Figure 5B:
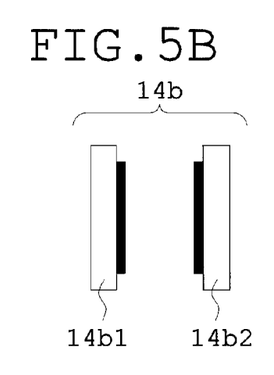
FIG. 5B is a view showing a distance between the surfaces of a pair of optical substrates and the angles of inclinations of the optical substrates in the second control of the variable spectral element, the optical substrates constituting a variable spectral element.
Figure 5C:
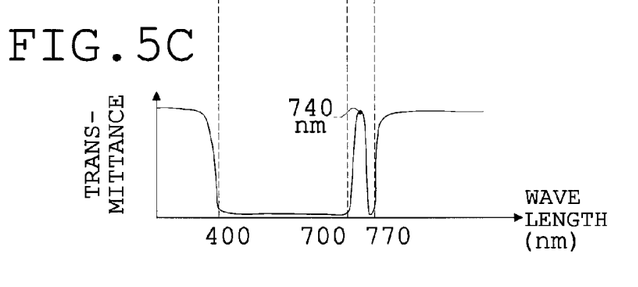
FIG. 5C is a graph showing a spectral transmittance of the variable spectral element in the second control.

FIGS. 5A to 5C are explanatory views showing one example of optical characteristics in a special light observation using an endoscope provided with an apparatus for obtaining spectral image with which a method for obtaining spectral image according to a variation example 2 of the embodiment 1 of the present invention is performed, FIG. 5A is a graph showing spectra of illumination light, FIG. 5B is a view showing a distance between the surfaces of a pair of optical substrates and angles of inclinations of the optical substrates in the second control of the variable spectral element, the optical substrates constituting a variable spectral element, and FIG. 5C is a graph showing a spectral transmittance of the variable spectral element in the second control.

In the apparatus for obtaining spectral image and the method for obtaining spectral image of the variation example 2, the variable spectral element control unit 13 is configured to control the variable spectral element 14b to widen a distance between the surfaces of the pair of the optical substrates 14b1 and 14b2 to a predetermined distance with the optical substrates 14b1 and 14b2 kept parallel to each other in the second control of the variable spectral element so that the transmission peak of the variable spectral element 14b shifts to a predetermined range of wavelengths longer than those of visible light reflected by the object 10 (the transmission peak of the variable spectral element 14b shifts to 740 nm in the variation example 2), the range of the wavelengths of the visible light reflected by the object 10 ranging from 400 nm to 700 nm, and the predetermined range of wavelengths longer than those of the visible light reflected by the object 10 being out of the range of the wavelengths of the visible light reflected by the object 10.

According to the apparatus for obtaining spectral image and the method for obtaining spectral image of the variation example 2, the variable spectral element 14b has a spectral characteristic in which its transmission peak is in a predetermined range of wavelengths longer than those of the light traveling from the object 10 (for example, its transmission peak is located at 740 nm in FIG. 5C) in the second control of the variable spectral element, the predetermined range of the wavelengths longer than those of the light from the object 10 being out of the range of the wavelengths of the light traveling from the object 10. However, light incident on the variable spectral element 14b is in the range of the wavelengths of the visible light reflected by the object 10 which ranges from 400 nm to 700 nm, so that no light incident on the variable spectral element 14b exists in the range of wavelengths longer than those of the visible light which range from 400 nm to 700 nm.

Accordingly, light incident on the variable spectral element 14b can be intercepted except leak light even though the second control of the variable spectral element is performed by the variable spectral element control unit 13 as in the variation example 2. As a result, second images captured by the imaging sensor 14c and the image-forming unit 15a are formed only by the leak light, and gray levels caused by the leak light are removed from first images when the image operation unit 15d calculates a difference between gray levels in first and second images in each pixel.

The other constitution and operation effects in the present variation example are the approximately same as those of the apparatus for obtaining spectral image and the method for obtaining spectral image of the embodiment 1.

Variation Example 3

Figure 6A:
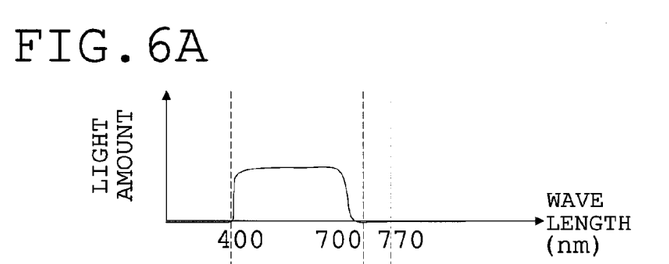
FIG. 6A is a graph showing spectra of illumination light.
Figure 6B:
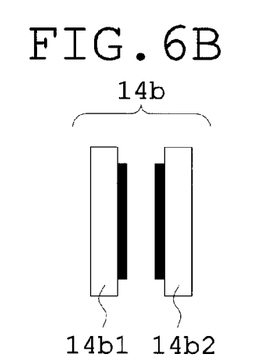
FIG. 6B is a view showing a distance between the surfaces of a pair of optical substrates and the angles of inclinations of the optical substrates in the second control of the variable spectral element, the optical substrates constituting a variable spectral element.
Figure 6C:
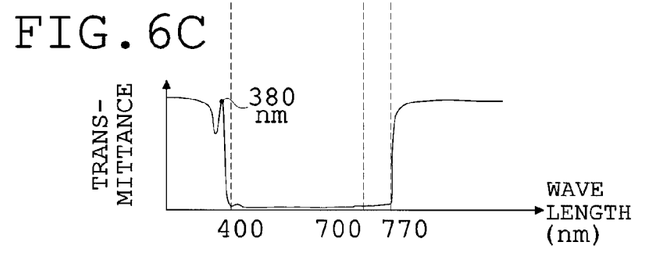
FIG. 6C is a graph showing a spectral transmittance of the variable spectral element in the second control.

FIGS. 6A, 6B, and 6C are explanatory views showing one example of optical characteristics in a special light observation using an endoscope provided with an apparatus for obtaining spectral image with which a method for obtaining spectral image according to a variation example 3 of the embodiment 1 of the present invention is performed, FIG. 6A is a graph showing spectra of illumination light, FIG. 6B is a view showing a distance between the surfaces of a pair of optical substrates and angles of inclinations of the optical substrates in the second control of the variable spectral element, the optical substrates constituting a variable spectral element, and FIG. 6C is a graph showing a spectral transmittance of the variable spectral element in the second control.

In the apparatus for obtaining spectral image and the method for obtaining spectral image of the variation example 3, the variable spectral element control unit 13 is configured to control the variable spectral element 14b to shorten a distance between the surfaces of the pair of the optical substrates 14b1 and 14b2 to a predetermined distance with the optical substrates 14b1 and 14b2 kept parallel to each other in the second control of the variable spectral element so that the transmission peak of the variable spectral element 14b shifts to a predetermined range of wavelengths shorter than those of visible light reflected by the object 10 to be imaged (the transmission peak of the variable spectral element 14b shifts to 380 nm in the variation example 3), the range of the wavelengths of the visible light reflected by the object 10 ranging from 400 nm to 700 nm, and the predetermined range of wavelengths shorter than those of the visible light reflected by the object 10 being out of the range of the wavelengths of the visible light reflected by the object 10.

According to the apparatus for obtaining spectral image and the method for obtaining spectral image of the variation example 3, the variable spectral element 14b has a spectral characteristic in which its transmission peak is in a predetermined range of wavelengths shorter than those of the light traveling from object 10 (for example, its transmission peak is located at 380 nm in FIG. 6C), in the second control of the variable spectral element, the predetermined range of the wavelengths shorter than those of the light from the object 10 being out of the range of the wavelengths of the light from the object 10. However, light incident on the variable spectral element 14b is in the range of the wavelengths of the visible light reflected by the object 10 which ranges from 400 nm to 700 nm, so that no light incident on the variable spectral element 14b exists in the range of wavelengths shorter than those of the visible light which range from 400 nm to 700 nm.

Accordingly, light incident on the variable spectral element 14b can be intercepted except leak light even though the second control of the variable spectral element is performed by the variable spectral element control unit 13 as in the variation example 3. As a result, second images captured by the imaging sensor 14c and the image-forming unit 15a are formed only by the leak light, and gray levels caused by the leak light are removed from first images when the image operation unit 15d calculates a difference between gray levels in first and second images in each pixel.

The other constitutions and operation effects in the present variation example are the approximately same as those of the apparatus and the method for obtaining spectral image according to the embodiment 1.

Variation Example 4

Figure 7A:
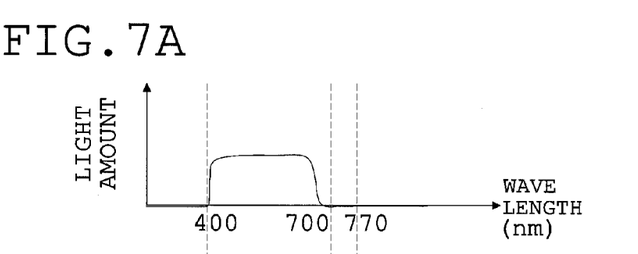
FIG. 7A is a graph showing spectra of illumination light.
Figure 7B:
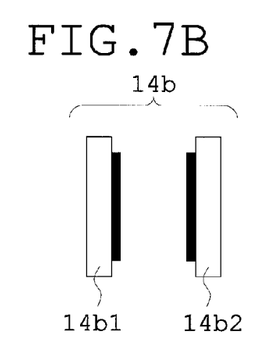
FIG. 7B is a view showing a distance between the surfaces of a pair of optical substrates and the angles of inclinations of the optical substrates in the second control of the variable spectral element, the optical substrates constituting a variable spectral element.
Figure 7C:
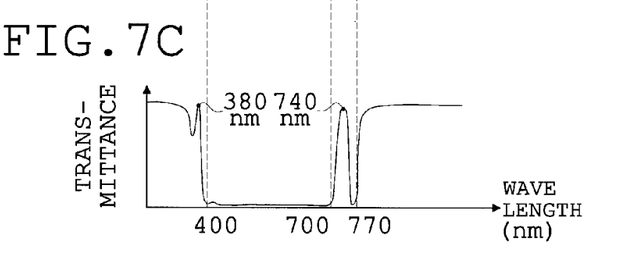
FIG. 7C is a graph showing a spectral transmittance of the variable spectral element in the second control.

FIGS. 7A, 7B, and 7C are explanatory views showing one example of optical characteristics in a special light observation using an endoscope provided with an apparatus for obtaining spectral image with which a method for obtaining spectral image according to a variation example 4 of the embodiment 1 of the present invention is performed, FIG. 7A is a graph showing spectra of illumination light, FIG. 7B is a view showing a distance between the surfaces of a pair of optical substrates and angles of inclinations of the optical substrates in the second control of the variable spectral element, the optical substrates constituting a variable spectral element, and FIG. 7C is a graph showing a spectral transmittance of the variable spectral element in the second control.

In the apparatus for obtaining spectral image and the method for obtaining spectral image of the variation example 4, the variable spectral element control unit 13 is configured to control the variable spectral element 14b to separate the pair of the optical substrates 14b1 and 14b2 from each other at a predetermined distance with the optical substrates 14b1 and 14b2 kept parallel to each other in the second control of the variable spectral element so that two transmission peaks of the variable spectral element 14b shift to a predetermined range of wavelengths shorter than those of visible light reflected by the object 10 to be imaged (one transmission peak shifts to 380 nm in the variation example 4) and to a predetermined range of wavelengths longer than those of the visible light reflected by the object 10 (the other transmission peak shifts to 740 nm in the variation example 4) respectively, the range of the wavelengths of the visible light reflected by the object 10 ranging from 400 nm to 700 nm, the predetermined ranges of the wavelengths shorter than those of the visible light reflected by the object 10 and of the wavelengths longer than those of the visible light reflected by the object 10 being out of the range of the wavelengths of the visible light reflected by the object 10.

According to the apparatus for obtaining spectral image and the method for obtaining spectral image of the variation example 4, the variable spectral element 14*b* has a spectral characteristic in which the two transmission peaks of the variable spectral element 14*b* are located in a predetermined range of wavelengths shorter than those of the light from the object 10 (for example, one transmission peak is located at 380 nm in FIG. 7C) and in a predetermined range of wavelengths longer than those of the light from the object 10 (for example, the other transmission peak is located at 740 nm in FIG. 7C) respectively, in the second control of the variable spectral element, the predetermined ranges of the wavelengths shorter than those of the light from the object 10 and of the wavelengths longer than those of the light from the object 10 being out of the range of the wavelengths of the light from the object 10. However, light incident on the variable spectral element 14*b* is in the range of the wavelength of the visible light reflected by the object 10 which ranges from 400 nm to 700 nm, so that light incident on the variable spectral element 14*b* exists neither in the range of wavelengths shorter than those of the visible light reflected by the object 10 nor in the range of wavelengths longer than those of the visible light reflected by the object 10, the range of the wavelengths of the visible light reflected by the object 10 ranging from 400 nm to 700 nm.

Accordingly, light incident on the variable spectral element 14*b* can be intercepted except leak light even though the second control of the variable spectral element is performed by the variable spectral element control unit 13 as in the variation example 4. As a result, second images captured by the imaging sensor 14*c* and the image-forming unit 15*a* are formed only by the leak light, and gray levels caused by the leak light are removed from first images when the image operation unit 15*d* calculates a difference between gray levels in first and second images in each pixel.

The other constitutions and operation effects in the present variation example are the approximately same as those of the apparatus for obtaining spectral image and the method for obtaining spectral image of the embodiment 1.

Besides, in the embodiment 1 and the variation examples 1 to 4, the first control and second control performed by the variable spectral element control unit 13 are changed to each other as often as the imaging sensor 14*c* captures one frame of an image, as described above, so that first images (narrow band image) and second images (reference image) are captured alternately the first images with the second images by the imaging sensor 14*c* and the image-forming unit 15*a*. However, timing for capturing the second images (reference image) in the present invention is not limited to such timing.

In the case where a user wants to capture a plurality of narrow band images with various wavelengths for example, the variable spectral element control unit 13 may change the first control of the variable spectral element and the second control of the variable spectral element to each other with timing at which one set of a plurality of the narrow band images is captured to be paired with a reference image in such a way that a second image (reference image) is captured by the imaging sensor 14*c* and the image-forming unit 15*a* after the narrow band images are captured as a first image, the narrow band images differing from one another in wavelengths with which the narrow band images are formed respectively.

Also, for example, a frequency at which first images (narrow band image) are captured may be made to differ from a frequency at which second images (reference image) are captured, in accordance with objects 10 to be imaged. In the case where a relatively-fast moving object is observed as in observation of a large intestine for example, the variable spectral element control unit 13 may change the first control of the variable spectral element and the second control of the variable spectral element to each other with timing at which first images (narrow band image) and second images (reference image) are captured alternately the first images with the second images by the imaging sensor 14*c* and the image-forming unit 15*a*. In the case where a relatively-slow moving object is observed as in observation of the inside of a mouth for example, the variable spectral element control unit 13 may change the first control of the variable spectral element and the second control of the variable spectral element to each other so that first images (narrow band image) and second images (reference image) are captured with timing at which one second image (reference image) is captured after a plurality of first images (narrow band image) are captured.

Also, these above-described timings for capturing second images (reference image) may be preset in an apparatus according to the present invention. Alternatively, an apparatus according to the present invention may be configured in such a way that: its input unit 12 is provided with a unit 7 for setting timing for obtaining second image for setting a timing with which a first image (spectral image) and a second image (reference image) are captured by the imaging sensor 14*c* and the image-forming unit 15*a* in order to enable users to set a timing with which a second image (reference image) is captured, the unit 7 for setting timing for obtaining second image having been explained in the example shown in FIG. 1; and the variable spectral element control unit 13 changes the first control of the variable spectral element and the second control of the variable spectral element to each other while synchronizing with a timing set through the unit for setting timing for obtaining second image.

Embodiment 2

Figure 8:
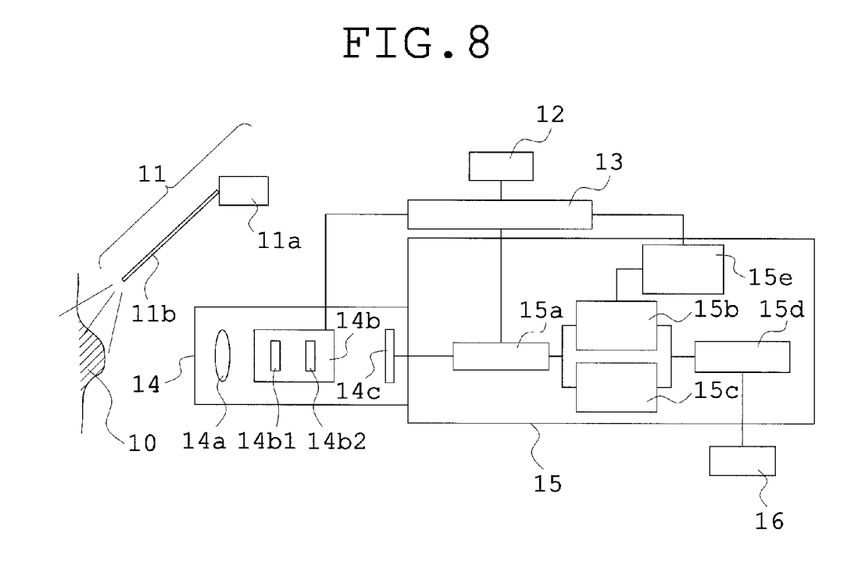
FIG. 8 is a block diagram showing the whole structure of an endoscope provided with an apparatus for obtaining spectral image with which a method for obtaining spectral image according to an embodiment 2 of the present invention is performed.

FIG. 8 is a block diagram showing the whole structure of an endoscope provided with an apparatus for obtaining spectral image with which a method for obtaining spectral image according to an embodiment 2 of the present invention is performed.

The apparatus for obtaining spectral image of the embodiment 2 according to the present invention not only has the structure of the embodiment 1 but also includes an image shift detecting unit 15*e* which is provided for the image-processing unit 15.

The image shift detecting unit 15*e* corresponds to the image shift detecting unit 6 shown in FIG. 1. And, the image shift detecting unit 15*e* is configured to detect an amount of a difference between a position of the object 10 in a standard image and a position of the object 10 in a first image that is captured by the image capturing units (the imaging sensor 14*c* and the image-forming unit 15*a*) after capturing the standard image, the standard image being a first image that is captured by the image capturing units for the first time after capturing a second image (reference image). Specifically, an edge of the object 10 in each image is detected, and a position difference amount in coordinates in which the edge is detected is detected as the number of pixels, for example. Alternatively, an amount of a variation in a gray level on each of predetermined coordinates in an image is detected. As described above, the image shift detecting unit 15e for the embodiment 2 is configured to detect an amount of a difference in positions of the object 10 in a publically-known manner.

Also, the variable spectral element control unit 13 is configured to operate in such a way that: when the amount of the difference in position of the object 10 detected by the image shift detecting unit 15e is beyond a predetermined threshold (an amount of a difference in edge of one to about several pixels, for example), the variable spectral element control unit 13 changes the first control of the variable spectral element to the second control of the variable spectral element and then changes the second control to the first control after the image capturing units (the imaging sensor 14c and the image-forming unit 15a) capture a second image.

In the apparatus for obtaining spectral image and the method for obtaining spectral image of the embodiment 1 according to the present invention, if a position of the object 10 in a first image differs from a position of the object 10 in a second image, then it is impossible to remove components of leak light contained in spectral images even though the image operation unit 15d calculates a difference between the first image and the second image.

On the other hand, it is desirable to decrease a frequency of capture of second images to the utmost in order to capture first images at a high frame rate. For example, in the case where the object 10 moves slowly, the position of the object 10 does not vary in a plurality of images, as described above. While it is desirable to capture a large number of first images (spectral image) to the utmost in order to increase a frame rate for an object to be observed, it is sufficient to capture one second image (reference image), in a plurality of images in which the position of the object does not vary.

Also, in the case where the moving speed of the object varies in observation of the object for example, it is impossible to capture second images efficiently. And, a difference between positions of the object 10 in a first image and a second image occurs or there easily occurs a situation where more second images than necessary are liable to be captured, so that an accuracy at which components from leak light are removed from a spectral image deteriorates or its frame rate easily lowers.

However, according to the apparatus for obtaining spectral image and the method for obtaining spectral image of the embodiment 2, it is possible to capture spectral images in such a way that: one second image is captured only when the position of a moving object varies to the extent that the movement of the object has a bad influence upon a calculation of a difference image between a first image and a second image which is calculated by the image operation unit 15d; and otherwise a first image is captured. As a result, spectral images from which components from leak light are removed at a high accuracy can be captured at a high frame rate regardless of whether the object moves fast or slowly.

Besides, in the apparatuses for obtaining spectral image and the methods for obtaining spectral image according to the present invention which are explained using the above-described embodiments respectively, the image operation unit 15d as an image correction unit has only to merely calculate a difference image between a first image and a second image which are formed by the image-forming unit 15a in the case where first images (spectral image) have the same imaging conditions (such as exposure time) as second images (reference image) do.

On the other hand, the image operation unit 15d as an image correction unit should calculate a difference image between a first image (spectral image) and a second image (reference image) after the second image (reference image) is given a predetermined operation process for correction so that the first image (spectral image) and the second image (reference image) become images that are captured under the approximately same imaging conditions in the case where the first image (spectral image) is different from the second image (reference image) in imaging conditions (for example, such as exposure time).

A predetermined operation process for correction may be performed, for example, in such a way that, in the case where exposure time for which a first image (spectral image) is captured is 20 milliseconds and exposure time for which a second image (reference image) is captured is 10 milliseconds, a gray level in each pixel of a second image (reference image) that is captured by the image-forming unit 15a is doubled so that a corrected second image (corrected reference image) is produced.

Afterward, a difference between the first image (spectral image) and the corrected second image is acquired.

Besides, when an operation process for correction is performed in this case, it is desirable to correct the second image while gray levels that are derived from fixed noise having no relation to whether exposure time is long or short are being let be (or a gray level derived from the fixed noise in each pixel is not doubled in the above-described example), the fixed noise being for example readout noise (that is noise arising in reading an electric signal from the imaging sensor 14c).

Up to now, the embodiments and embodied examples of apparatuses for obtaining spectral image and method for obtaining spectral image according to the present invention have been explained. However, the present invention is not limited to these embodiments and embodied examples, and an apparatus for obtaining spectral image and a method for obtaining spectral image according to the present invention may be configured in a combination of the characteristic structures of the above-described embodiments and embodied examples. Also, the above-described embodied examples are explained as examples which are preferable to an observation through reflection light having specific narrowband wavelengths in a visible light wavelength range with an endoscope. However, an apparatus for obtaining spectral image and a method for obtaining spectral image according to the present invention can be also used for a fluorescence observation through specific wavelengths in a visible light wavelength range or a near-infrared fluorescence observation. For example, in the case of a fluorescence observation like a near-infrared fluorescence observation, light traveling from an object to be photographed has a wavelength of excitation light reflected by the object and a wavelength of fluorescence emitting from the object. In this case, a variable spectral element control unit should be made to control a distance between the surfaces of a pair of optical substrates of a variable spectral element and angles of inclinations of the optical substrates so that: the variable spectral element has a spectral characteristic in which the transmission peak of the variable spectral element exists near the wavelength of the fluorescence, in the first control of the variable spectral element; and the variable spectral element has a spectral characteristic in which the transmission peak of the variable spectral element exists neither in a range of wavelengths of the excitation light reflected by the object nor in a range of wavelengths of the fluorescence emitting from the object, in the second control of the variable spectral element.

Also, an apparatus for obtaining spectral image and a method for obtaining spectral image according to the present invention are applicable not only to endoscopes but also to observation apparatuses by which a spectral observation is performed, such as microscopes and surveillance cameras.

An apparatus for obtaining spectral image and a method for obtaining spectral image according to the present invention are useful for observation apparatuses in which objects to be photographed are observed through their spectral images using etalon-type variable spectral elements respectively.

What is claimed is:

1. An apparatus comprising:
a variable spectral element comprising a pair of optical substrates placed opposite each other on an optical path of light from an object, wherein the variable spectral element is configured to change its spectral characteristic by changing at least one of a distance between surfaces of the pair of optical substrates and angles of inclinations of the surfaces of the pair of optical substrates;
a variable spectral element controller configured to change between a first control of the variable spectral element and a second control of the variable spectral element,
wherein under the first control, the variable spectral element controller is configured to control the variable spectral element such that the surfaces of the pair of optical substrates are parallel with each other at a predetermined distance so that the variable spectral element has a first spectral characteristic comprising a transmission peak in a preset wavelength range and a first leak light transmittance in a first wavelength range different from the preset wavelength range, and
wherein under the second control, the variable spectral element controller is configured to control the variable spectral element such that the surfaces of the pair of optical substrates are at least one of non-parallel to each other and nearer or farther to each other than the predetermined distance, so that the variable spectral element has a second spectral characteristic comprising a second leak light transmittance in a second wavelength range different from the preset wavelength range and at least partially overlapping the first wavelength range, and not comprising the transmission peak in the preset wavelength range;
an image sensor configured to capture:
a first image that is formed by light transmitted by the variable spectral element under the first control; and
a second image that is formed by light transmitted by the variable spectral element under the second control; and
an image processor configured to acquire a difference image based on a difference between the first image and the second image.

2. The apparatus according to claim 1,
wherein under the second control, the variable spectral element controller is configured to set angles of inclinations of the surfaces of the pair of the optical substrates to predetermined angles at which the surfaces of the pair of optical substrates are not parallel to each other.

3. The apparatus according to claim 2,
wherein the image processor is configured to detect an amount of a difference between a position of the object in a standard image and a position of the object in the first image captured by the image sensor after capturing the standard image,
wherein the variable spectral element controller is configured to change from the first control of the variable spectral element to the second control of the variable spectral element when the amount of the difference between the positions of the object in the standard image and the first image is beyond a predetermined threshold, and
wherein the variable spectral element controller is configured to change from the second control to the first control after the image sensor captures the second image.

4. The apparatus according to claim 2,
wherein the variable spectral element controller is configured to change between the first control of the variable spectral element and the second control of the variable spectral element with timing at which the image sensor can capture the first image and the second image alternately.

5. The apparatus according to claim 2,
wherein the variable spectral element controller is configured to change between the first control of the variable spectral element and the second control of the variable spectral element at a preset timing.

6. The apparatus according to claim 1,
wherein under the second control, the variable spectral element controller is configured to widen the distance between the surfaces of the pair of optical substrates beyond the predetermined distance.

7. The apparatus according to claim 1,
wherein under the second control, the variable spectral element controller is configured to control the variable spectral element to change the distance between the surfaces of the pair of optical substrates to be different from the predetermined distance and the angles of inclinations of the surfaces of the pair of optical substrates to predetermined angles so that the second spectral characteristic comprises a transmission peak in a wavelength range outside of the wavelength range of the light from the object.

8. The apparatus according to claim 1,
wherein the image processor is configured to detect an amount of a difference between a position of the object in a standard image and a position of the object in the first image captured by the image sensor after capturing the standard image,
wherein the variable spectral element controller is configured to change from the first control of the variable spectral element to the second control of the variable spectral element when the amount of the difference between the positions of the object in the standard image and the first image is beyond a predetermined threshold, and
wherein the variable spectral element controller is configured to change from the second control to the first control after the image sensor captures the second image.

9. The apparatus according to claim 1,
wherein the variable spectral element controller is configured to change between the first control of the variable spectral element and the second control of the variable spectral element with timing at which the image sensor can capture the first image and the second image alternately.

10. The apparatus according to claim 1,
wherein the variable spectral element controller is configured to change between the first control of the variable spectral element and the second control of the variable spectral element at a preset timing.

11. The apparatus according to claim 1,
wherein the image processor is configured to calculate a difference between a gray level of the first image captured under the first control and a gray level of the second image captured under the second control.

12. The apparatus according to claim 1,
wherein under the first control, the variable spectral element controller is configured to control the variable spectral element such that the light transmitted by the variable spectral element and forming the first image contains components in the preset wavelength range, within which a desired wavelength exists, and components of first leak light, which are in the first wavelength range different from the preset wavelength range, and
wherein under the second control, the variable spectral element controller is configured to control the variable spectral element such that the light transmitted by the variable spectral element and forming the second image contains components of second leak light, which are in the second wavelength range, amounts of the components of the second leak light being approximately equal to amounts of the components of the first leak light.

13. The apparatus according to claim 12,
wherein under the second control, the variable spectral element controller is configured to control the variable spectral element such that the light transmitted by the variable spectral element and forming the second image contains the components of the second leak light alone.

14. A method comprising:
providing a variable spectral element comprising a pair of optical substrates placed opposite each other on an optical path of light from an object, wherein the variable spectral element is configured to change its spectral characteristic by changing at least one of a distance between surfaces of the optical substrates and angles of inclinations of the surfaces of the pair of optical substrates;
changing between a first control of the variable spectral element and a second control of the variable spectral element,
wherein under the first control, the variable spectral element is controlled such that the surfaces of the pair of optical substrates are parallel with each other at a predetermined distance so that the variable spectral element has a first spectral characteristic comprising a transmission peak in a preset wavelength range and a first leak light transmittance in a first wavelength range different from the preset wavelength range, and
wherein under the second control, the variable spectral element is controlled such that the surfaces of the pair of optical substrates are at least one of non-parallel to each other and nearer or farther to each other than the predetermined distance so that the variable spectral element has a second spectral characteristic comprising a second leak light transmittance in a second wavelength range different from the preset wavelength range and at least partially overlapping the first wavelength range, and not comprising the transmission peak in the preset wavelength range;
capturing:
a first image formed by light that is transmitted by the variable spectral element under the first control; and
a second image formed by light transmitted by the variable spectral element under the second control; and
acquiring a difference image based on a difference between the first image and the second image.

15. The method according to claim 14,
wherein under the second control of the variable spectral element, the surfaces of the pair of the optical substrates are inclined at predetermined angles at which the surfaces of the pair of optical substrates are not parallel to each other.

16. The method according to claim 14,
wherein under the second control of the variable spectral element, the distance between the surfaces of the pair of optical substrates is widened beyond the predetermined distance.

17. The method according to claim 14,
wherein under the second control of the variable spectral element, the distance between the surfaces of the pair of optical substrates is controlled to be different from the predetermined distance and the angles of inclinations of the surfaces of the pair of optical substrates are controlled to change to predetermined angles respectively.

18. The method according to claim 14, further comprising:
detecting an amount of a difference between a position of the object in a standard image and a position of the object in the first image captured after capturing the standard image,
changing from the first control of the variable spectral element to the second control of the variable spectral element so that a second image is captured when the amount of the difference between the positions of the object in the standard image and the first image is beyond a predetermined threshold, and
changing from the second control to the first control after capturing the second image.

19. The method according to claim 14, further comprising:
changing between the first control of the variable spectral element and the second control of the variable spectral element with timing at which the first image and second image can be captured alternately.

20. The method according to claim 14,
wherein changing between the first control of the variable spectral element and the second control of the variable spectral element comprises changing between the first control and second control at a preset timing.

* * * * *